United States Patent
Ilan et al.

(10) Patent No.: US 11,426,483 B2
(45) Date of Patent: Aug. 30, 2022

(54) WOUND DRESSING AND A METHOD FOR PRODUCING THE SAME

(71) Applicant: Omrix Biopharmaceuticals Ltd., Rehovot (IL)

(72) Inventors: Erez Ilan, Kibbutz Netzer Sereni (IL); Omri Faingold, Rehovot (IL)

(73) Assignee: Omrix Biopharmaceuticals Ltd., Kiryat-Ono (IL)

( * ) Notice: Subject to any disclaimer, the term of this patent is extended or adjusted under 35 U.S.C. 154(b) by 363 days.

(21) Appl. No.: 16/195,898

(22) Filed: Nov. 20, 2018

(65) Prior Publication Data

US 2019/0184052 A1 Jun. 20, 2019

Related U.S. Application Data

(60) Provisional application No. 62/607,497, filed on Dec. 19, 2017.

(30) Foreign Application Priority Data

Dec. 19, 2017 (IL) .......................................... 256405

(51) Int. Cl.
| | | |
|---|---|---|
| A61L 26/00 | (2006.01) | |
| A61L 15/32 | (2006.01) | |
| A61F 13/02 | (2006.01) | |
| A61F 13/00 | (2006.01) | |
| A61L 15/42 | (2006.01) | |
| A61F 17/00 | (2006.01) | |
| A61L 31/04 | (2006.01) | |

(52) U.S. Cl.
CPC ........ *A61L 15/32* (2013.01); *A61F 13/00012* (2013.01); *A61F 13/00063* (2013.01); *A61F 13/00991* (2013.01); *A61F 13/0203* (2013.01); *A61F 13/0289* (2013.01); *A61F 17/00* (2013.01); *A61L 15/425* (2013.01); *A61F 13/0253* (2013.01); *A61F 2013/00931* (2013.01); *A61L 31/046* (2013.01); *A61L 2400/04* (2013.01)

(58) Field of Classification Search
CPC ...... C08L 1/04; C08L 1/02; C08L 1/00; C08L 2203/16; A61L 31/042; A61L 15/325; A61L 15/28; A61L 31/041; A61L 15/44; A61L 15/64; A61L 31/10; A61L 15/42; A61L 15/56; A61F 13/0226; A61F 2/0063; A61F 13/00995; A61F 13/0203; A61F 13/0206; A61F 13/0209; A61F 13/0213; A61F 13/0256; A61F 13/069; A61F 2013/00463
See application file for complete search history.

(56) References Cited

U.S. PATENT DOCUMENTS

| | | | |
|---|---|---|---|
| 7,186,684 B2 * | 3/2007 | Pendharkar | A61L 15/32 424/445 |
| 2006/0088589 A1 | 4/2006 | Gorman | |
| 2011/0152924 A1 | 6/2011 | Gensini et al. | |
| 2012/0209319 A1 * | 8/2012 | Bianco-Peled | A61L 24/0094 606/213 |
| 2015/0017225 A1 * | 1/2015 | Hubbell | A61L 15/64 424/444 |

FOREIGN PATENT DOCUMENTS

| | | |
|---|---|---|
| CN | 1181979 A | 5/1998 |
| CN | 101084021 A | 12/2007 |
| CN | 101516301 A | 8/2009 |
| CN | 101716383 A | 6/2010 |
| CN | 104721878 A | 6/2015 |
| EP | 0534178 | 4/2001 |
| EP | 1390485 | 10/2006 |
| EP | 1802358 A2 | 7/2007 |
| WO | 2005016116 A2 | 2/2005 |
| WO | 2013001524 A1 | 1/2013 |

OTHER PUBLICATIONS

Anonymous: "Combination of a liquid fibrin sealant with sheet-type hemostatic agents: Experimental evaluation in partial nephrectomy animal model—Ishii—2011—International Journal of Urology—Wiley Online Library" Apr. 13, 2011, XP055565919, URL:https://onlinelibrary.wiley.com/doi/epef/10.1111/j.1442-2042.2011.02767.x retrieved on Mar. 7, 2019.
Deanglis, et al., A method to measure thrombin activity in a mixture of fibrinogen and thrombin powders, Blood Coagulation and Fibrinolysis, 2017, pp. 134-138, vol. 28 Issue 2.
International, International Search Report & Written Opinion, ISR &WO, dated Jul. 27, 2019, pp. 9, No. Volume, IB.
Ishii et al., Basic in Vitro Experiment on the Adhesive Effects of Sheet-Type Hemostatic Agents Used in Combination with a Liquid Fibrin Sealant, Journal of Endourology, 2011, pp. 1775-1779, vol. 25, No. 11.
Ishii et al., Combination of a Liquid Fibrin Sealant with Sheet-Type Hemostatic Agents: Experimental Evaluation in Partial Nephrectomy Animail Model, International Journal of Urology, 2011, pp. 478 482, vol. 18 No. 6.
Lewis, et al., Comparison of Regenerated and Non-Regenerated Oxidized Cellulose Hemostatic Agents, European Surgery, 2013, pp. 213-220, vol. 45, No. 4.
MacDonald, et al., An in vivo comparison of the efficacy of hemostatic powders, using two porcinebleeding models, Medical Devices: Evidence and Research, 2017, pp. 273-279, vol. 10.

(Continued)

*Primary Examiner* — Susan T Tran
(74) *Attorney, Agent, or Firm* — David R. Crichton (57) ABSTRACT

The invention provides a wound dressing made by an ex vivo formed combination of fibrinogen and/or fibrin containing-liquid formulation and an oxidized cellulose (OC) backing; and use thereof.

11 Claims, 1 Drawing Sheet

(56) References Cited

OTHER PUBLICATIONS

Spangler, et al., In Vitro Antimicrobial Activity of Oxidized Regenerated Cellulose Against Antibiotic-Resistant Microorganisms, Surgical Infections, 2003, pp. 255-262, vol. 4, No. 3.

* cited by examiner

WOUND DRESSING AND A METHOD FOR PRODUCING THE SAME

TECHNOLOGICAL FIELD

The present disclosure relates, inter alia, to therapeutic devices and methods for treating wounds.

BACKGROUND

References considered to be relevant as background to the presently disclosed subject matter are listed below.

Acknowledgement of the above references herein is not to be inferred as meaning that these are in any way relevant to the patentability of the presently disclosed subject matter.

The control of bleeding is essential and critical in surgical procedures to minimize blood loss, to reduce post-surgical complications, and to shorten the duration of the surgery in the operating room. Topical Absorbable Hemostats (TAH) are one option for managing and controlling bleeding that are widely used in surgical applications.

Relevant prior art references are: Ishii, Keiichi, et al. *Journal of Endourology,* 25 (11), 1775-1779 (2011); Ishii, Keiichi, et al. *International Journal of Urology* 18(6), 478-482 (2011), Lewis, K. M., et al. *European Surgery* 45(4), 213-220 (2013); Spangler, Daniel et al. *Surgical Infections* 4(3), 255-262 (2003); and DeAnglis, Ashley P. et al. *Blood Coagulation & Fibrinolysis* 28, 134-138 (2017).

US Patent application, publication No. 2012/0209319, describes a reinforced multi component adhesive comprising layer of uncured and curable composition of matter, and a biocompatible inert reinforcing agent comprising at least one curing agent and a thin film, e.g. oxidized regenerated cellulose.

GENERAL DESCRIPTION

The present disclosure provides, in accordance with a first of its aspects, a method for producing a wound dressing to be applied to a tissue comprising a liquid formulation comprising fibrinogen and/or fibrin (the liquid formulation is also referred to as: "fibrinogen and/or fibrin-containing liquid formulation", interchangeably) with an oxidized cellulose (OC) backing which are ex vivo combined to thereby obtain the wound dressing.

According to an aspect of the present invention, there is provided a method for producing wound dressing to be applied onto a tissue, the method comprising ex vivo combining a liquid formulation comprising fibrinogen and/or fibrin with an oxidized cellulose (OC) backing to thereby obtain the wound dressing.

In some embodiments of the method, the OC backing has a wound facing side and the liquid formulation is combined at least with the wound facing side.

In some embodiments of the method, the wound dressing is to be applied to a tissue within less than 20 second from the combining.

In some embodiments of the method, the OC backing comprises oxidized regenerated cellulose (ORC).

In some embodiments of the method, the OC backing is in the form of a knitted, woven or non-woven fabric.

In some embodiments of the method, the liquid formulation comprises thrombin.

In some embodiments of the method, the combining comprises any one of: spraying, smearing, brushing, casting, printing, injecting and soaking the liquid formulation.

In some embodiments of the method, the thrombin is present at a concentration ranging from 400 to 1200 IU/ml.

In some embodiments of the method, the fibrinogen and/or fibrin are present at a concentration ranging from 10 to 120 mg/ml.

According to a further aspect of the present invention, there is provided a wound dressing comprising an ex vivo formed combination of a liquid formulation comprising fibrinogen and/or fibrin (i.e. fibrinogen and/or fibrin containing-liquid formulation) and an oxidized cellulose (OC) backing.

In some embodiments of the wound dressing, the liquid formulation is combined at least partially with a wound facing side of the wound dressing.

In some embodiments of the wound dressing, the OC backing comprises oxidized regenerated cellulose (ORC).

In some embodiments of the wound dressing, the OC backing is in the form of a knitted, woven or non-woven fabric.

In some embodiments of the wound dressing, the liquid formulation further comprises thrombin.

In some embodiments of the wound dressing, the thrombin is present at a concentration ranging from 400 to 1200 IU/ml.

In some embodiments of the wound dressing, the fibrinogen and/or fibrin are present at a concentration ranging from 10 to 120 mg/ml.

In some embodiments of the wound dressing, the liquid formulation is sprayed, smeared, brushed, casted, printed or soaked within the backing.

In the relevant context of the present disclosure, when referring to "combined", or any grammatical inflection thereof, it is to be understood as any form of association/ contacting between the liquid formulation and OC backing. This may include, without being limited thereto, any one or combination of spraying, smearing, dipping, soaking, brushing, casting, printing, injecting, coating, as further described below.

In accordance with yet another aspect, there is also provided by the present disclosure, a method of treating (also referred to as: "the treatment method") a wounded tissue in a subject, the method comprising:

(a) ex vivo combining a liquid formulation comprising fibrinogen and/or fibrin with an oxidized cellulose (OC) backing to form a wound dressing; and (b) applying the wound dressing onto a wound, the applying being carried out within less than 20 seconds from the combining.

In some embodiments of the treatment method, the OC backing has a wound facing side and the liquid formulation is combined at least with the wound facing side, wherein the wound facing side is applied onto the wounded tissue.

In some embodiments of the treatment method, the wounded tissue is a bleeding tissue.

In some embodiments of the treatment method, the backing comprises oxidized regenerated cellulose (ORC).

In some embodiments of the treatment method, the OC backing is in the form of a knitted, woven or non-woven fabric.

In some embodiments of the treatment method, the formulation further comprises thrombin.

In some embodiments of the treatment method, the thrombin is present at a concentration ranging from 400 to 1200 IU/ml.

In some embodiments of the treatment method, the fibrinogen and/or fibrin are present at a concentration ranging from 10 to 120 mg/ml.

In some embodiments of the treatment method, the combining comprises any one of spraying, smearing, brushing, casting, printing, injecting and soaking of the liquid formulation.

In some embodiments of the treatment method, the method further comprises pressing the wound dressing against the wounded tissue.

In some embodiments of the treatment method, the pressing is carried out for a time sufficient to allow adherence of the wound dressing to at least a portion of the wounded tissue.

In some embodiments of the treatment method, the subject is a human subject.

In some embodiments of the treatment method, the method is for treating a wound during a surgical procedure.

In some embodiments of the treatment method, the surgical procedure comprises abdominal surgery, cardiovascular surgery, thoracic surgery, head and neck surgery, pelvic surgery, skin and subcutaneous tissue procedure.

In some embodiments of the treatment method, the wounded tissue comprises a bleeding artery.

In some embodiments of the treatment method, the treatment comprises reducing bleeding.

In accordance with a further aspect, there is provided by the present disclosure a kit for treating a wounded tissue in a subject comprising: a first container comprising an oxidized cellulose (OC) backing; and a second container comprising a formulation comprising fibrinogen and/or fibrin.

In some embodiments of the kit, the formulation is in a liquid or in a frozen form.

In some embodiments of the kit, the kit comprises instructions for ex vivo use of the OC backing in combination with the formulation.

In some embodiments of the kit, the OC backing comprises oxidized regenerated cellulose (ORC).

In some embodiments of the kit, the OC backing is in the form of a knitted, woven or non-woven fabric.

In some embodiments of the kit, the kit comprises thrombin within the second container.

In some embodiments of the kit, the thrombin is present at a concentration ranging from 400 to 1200 IU/ml.

In some embodiments of the kit, the fibrinogen and/or fibrin are present at a concentration ranging from 10 to 120 mg/ml.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWING

In order to better understand the subject matter that is disclosed herein and to exemplify how it may be carried out in practice, embodiments will now be described, by way of a non-limiting example only, with reference to the accompanying drawing, in which.

DETAILED DESCRIPTION OF EMBODIMENTS

During surgical procedures, a surgeon must be able to address homeostasis.

Topical Absorbable Hemostats (TAH) encompass products based on oxidized cellulose (OC), oxidized regenerated cellulose (ORC), gelatin, collagen, chitin, chitosan, etc. To improve the hemostatic performance, scaffolds based on the above materials can be combined with biologically-derived clotting factors, such as, and without being limited thereto, thrombin and fibrinogen.

The present disclosure is based on the realization that in many cases, especially when the bleeding in the wound is severe, when applying a biological glue, e.g. liquid fibrin/fibrinogen-based sealant, directly onto a bleeding tissue, the glue might be washed away or diluted by the flow of the blood and thus, be less effective in reducing the bleeding.

An object of the present disclosure is to overcome the drawback of co-administration of oxidized cellulose and thrombin and/or fibrinogen in view of the acidity of the oxidized cellulose. Such acidity immediately denatures plasma proteins (e.g., thrombin, fibrinogen, tissue factor, etc.). Therefore, co-administration of oxidized cellulose and thrombin, fibrinogen, or alike, might render these plasma proteins ineffective.

It was found according to the disclosure that, surprisingly, when the liquid sealant matter and specific kinds of TAH, such as ORC, are combined ex vivo, the bleeding rate is beneficially reduced, particularly if placed onto the wound within a specified time window from the combination of the same.

Herein, by "combined ex vivo" (or "ex vivo combined") it is meant that the step of combining the liquid sealant matter and the specific kind of TAH, such as ORC, is not employed upon a physical contact of either the sealant matter or the specific kind of TAH (e.g., ORC) with the bleeding site.

Accordingly, the present disclosure provides, in one aspect thereof, a method for producing a wound dressing to be applied to a tissue, the method comprising ex vivo combining a fibrinogen and/or fibrin-containing liquid formulation with an oxidized cellulose (OC) backing, such as, and without being limited thereto, an ORC backing, to thereby obtain the wound dressing.

In one such embodiment, the backing has a wound facing side surface and the liquid formulation is combined, at least partially with the wound facing side surface. Hereinthroughout, by "combined, at least partially with the wound facing side surface" it is meant that at least a portion of a surface of the wound facing side is combined with the liquid formulation.

In some such embodiments, the liquid formulation is in the form of a layer on the surface.

The thickness of the patch (e.g., pad) may be about 1 mm or above, such as about 45 mm, or, in some embodiments, may be about 1 to about 45 mm.

Accordingly, in some embodiments, the thickness of patch (e.g., pad) is 1, 2.5, 5, 10, 15, 20, 25, 30, 35, 40, or 45 mm, including any value and range therebetween.

In some embodiments, the term "at least a portion of the surface of the wound facing side" refers to at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or even 100% of the surface of the wound facing side.

In one embodiment, the wound dressing is to be applied or is configured be applied to a tissue within less than 20 second from the ex vivo combining.

In some embodiments, application of the wound dressing may be performed within 19, 18, 17, 16, 15, 14, 13, 12, 11, 10, 9, 8, 7, 6 5, 4, 3, 2, or 1 seconds or even immediately upon the combining. In some embodiments, the application onto the wound is carried out after at least 2 to 5 seconds from combining, or in some embodiments, after at least 2 to 10 seconds from combining.

The term "immediately" refers to around 0 seconds, for example from 0-2 seconds.

In some embodiments, the disclosed wound dressing is configured to be applied onto a tissue within 2 to 20 seconds from the combining. In some such embodiments, as further described in the Examples section below, the ex vivo combining of the liquid formulation with an OC (e.g., ORC) backing, provides a wound dressing characterized by adherence strength of at least 50% or at least 60%, e.g., at least 50%, at least 60%, at least 70%, at least 80%, or at least 90%, compared to the corresponding adherence strength provided upon in-situ preparation of fibrin sealant drip directly on the bleeding tissue and then combining with the OC (e.g., ORC).

In some embodiments, the ex vivo combining of the liquid formulation with an OC (e.g., ORC) backing, provides a wound dressing characterized by adherence strength of 50 to 90% compared to the corresponding adherence strength provided upon in-situ preparation of fibrin sealant drip directly on the bleeding tissue and then combining with the OC (e.g., ORC).

Herein, the term "adhesion strength" refers to the pull-force strength required to break the contact between the wound dressing and the tissue.

In a further embodiment, the backing comprises ORC.

In a further embodiment, the backing comprises ORC having an oxidation level ranging from 12 to 21%. In a further embodiment, the backing comprises ORC having an oxidation level ranging from 18 to 21%.

In a further embodiment, the backing comprises ORC having an oxidation level of 12, 13, 14, 15, 16, 17, 18, 19, 20, or 21%, including any value and range therebetween.

In some embodiments, the oxidation level refers to the carboxyl content of the ORC.

Methods for determining the oxidation level are known in the art. In exemplary embodiments, the oxidation level is determined per United States Pharmacopeia (USP) 23-NF18.

In a further embodiment, the backing is in the form of a knitted fabric.

In some embodiments, the backing is in the form of woven or non-woven fabric.

In a further embodiment, the formulation comprises thrombin.

In a further embodiment, the sealant formulation comprises a two-component formulation comprising: a thrombin component, such as, and without being limited thereto, a liquid thrombin component, and a fibrinogen component, such as, and without being limited thereto, a liquid fibrinogen component.

In a further embodiment, the sealant formulation comprises a two-component formulation comprising: a thrombin component, such as, and without being limited thereto, a liquid thrombin component, and a fibrin component, such as, and without being limited thereto, a liquid fibrin component.

In a further embodiment, the sealant formulation comprises a fibrin component, such as, and without being limited thereto, a liquid fibrin component.

In a further embodiment, the sealant formulation comprises a two-component formulation comprising: a thrombin component, such as, and without being limited thereto, a liquid thrombin component; and a component comprising fibrin and fibrinogen, such as, and without being limited thereto, a liquid fibrin-and-fibrinogen component.

In a further embodiment of the sealant formulation, the thrombin is present at a concentration of about 2 to 1200 IU/ml, 2.5 to 1200 IU/ml, 8 to 1200 IU/ml, 80 to 1200 IU/ml, 400 to 1200 IU/ml, 400 to 600 IU/ml, or 800 to 1200 IU/ml.

In a further embodiment of the sealant formulation, the thrombin is present at a concentration of about 2, 2.5, 3, 3.5, 4, 4.5, 5, 5.5, 6, 6.5, 7, 7.5, 8, 10, 50, 80, 100, 200, 300, 400, 500, 600, 700, 800, 900, 1000, 1100, or 1200 IU/ml, including any value and range therebetween.

In a further embodiment of the formulation, the thrombin is present at the thrombin component at concentration of about 2 to 1200 IU/ml, 2.5 to 1200 IU/ml, 8 to 1200 IU/ml, 80 to 1200 IU/ml, 400 to 1200 IU/ml, 400 to 600 IU/ml, or 800 to 1200 IU/ml.

In a further embodiment of the formulation, the thrombin is present at the thrombin component at a concentration of about 2, 2.5, 3, 3.5, 4, 4.5, 5, 5.5, 6, 6.5, 7, 7.5, 8, 10, 50, 80, 100, 200, 300, 400, 500, 600, 700, 800, 900, 1000, 1100, or 1200 IU/ml, including any value and range therebetween.

As used herein, the term "IU" denotes "International Units" and may be determined by the clotting assay against an internal reference standard for potency concentration measurement that has been calibrated against, for example, the World Health Organization (WHO) Second International Standard for Thrombin, 01/580. A unit (U) is equivalent to an International Unit (IU).

In a further embodiment of the sealant formulation, the fibrinogen is present at a concentration of about 10 to 120 mg/ml, 10 to 105 mg/ml, 25 to 90 mg/ml, 30 to 45 mg/ml, 60 to 90 mg/ml, 60 to 110 mg/ml, or 55 to 85 mg/ml.

In a further embodiment of the sealant formulation, the fibrinogen is present at a concentration of 10, 15, 20, 25, 30, 35, 40, 45, 50, 55, 60, 65, 70, 75, 80, 85, 90, 95, 100, 105, 110, 115, or 120 mg/ml, including any value and range therebetween.

In a further embodiment of the formulation, the fibrinogen is present at the fibrinogen component at a concentration of about 10 to 120 mg/ml, 10 to 105 mg/ml, 25 to 90 mg/ml, 30 to 45 mg/ml, 60 to 90 mg/ml, 60 to 110 mg/ml, or 55 to 85 mg/ml.

In a further embodiment of the formulation, the fibrinogen is present at the fibrinogen component at a concentration of 10, 15, 20, 25, 30, 35, 40, 45, 50, 55, 60, 65, 70, 75, 80, 85, 90, 95, 100, 105, 110, 115, or 120 mg/ml, including any value and range therebetween.

In some embodiments, the two components of the formulation (i.e. thrombin and fibrinogen) are combined in a ratio (v/v) ranging from about 1.5:1 to about 1:1.5. In some embodiments, the two components of the formulation (i.e.

thrombin and fibrinogen) are combined in a ratio (v/v) ranging from about 1.2:1 to about 1:1.2.

In exemplary embodiments the two components of the formulation (i.e. thrombin and fibrinogen) are combined in a ratio (v/v) of about 1:1.

In a further embodiment of the sealant formulation, the fibrin is present at a concentration of about 10 to 120 mg/ml, 10 to 105 mg/ml, 25 to 90 mg/ml, 30 to 45 mg/ml, 60 to 90 mg/ml, 60 to 110 mg/ml, or 55 to 85 mg/ml.

In a further embodiment of the sealant formulation, the fibrin is present at a concentration of 10, 15, 20, 25, 30, 35, 40, 45, 50, 55, 60, 65, 70, 75, 80, 85, 90, 95, 100, 105, 110, 115, or 120 mg/ml, including any value and range therebetween.

In a further embodiment of the formulation, the combination of fibrinogen and fibrin is present at a concentration of about 10 to 120 mg/ml, 10 to 105 mg/ml, 25 to 90 mg/ml, 30 to 45 mg/ml, 60 to 90 mg/ml, 60 to 110 mg/ml, or 55 to 85 mg/ml.

In a further embodiment of the formulation, the combination of fibrinogen and fibrin is present at a concentration of 10, 15, 20, 25, 30, 35, 40, 45, 50, 55, 60, 65, 70, 75, 80, 85, 90, 95, 100, 105, 110, 115, or 120 mg/ml, including any value and range therebetween.

In a further embodiment, the combining comprises one or more steps selected from: spraying, smearing, brushing, casting, printing, injecting and soaking the fibrinogen and/or fibrin containing liquid formulation.

Also provided by the present disclosure is:

a wound dressing comprising an ex vivo formed combination of fibrinogen and/or fibrin containing-liquid formulation and an oxidized cellulose (OC) backing, such as, and without being limited thereto, an ORC backing.

In one such embodiment, the backing has a wound facing side and the liquid formulation is combined, at least partially, with the wound facing side. In another embodiment, the wound dressing is to be applied to a tissue within less than 20 second from the combining. In a further embodiment, the backing is in the form of a knitted, woven or non-woven fabric.

In a further embodiment, the formulation comprises thrombin.

According to another aspect of the present invention, there is provided a method of treating a wounded tissue in a subject, the method comprising (a) ex vivo combining a fibrinogen and/or fibrin containing liquid formulation with a topical absorbable hemostat (TAH) backing or a scaffold comprising OC, such as, without limitation, ORC, to form a wound dressing; and (b) applying the wound dressing onto a wound, the application being within less than 20 seconds from the combining.

In one such embodiment of the treating method, the backing or scaffold has a wound facing side and the liquid formulation is combined at least partially with the wound facing side.

In one embodiment, the wounded tissue is a bleeding tissue.

In a further embodiment, the backing comprises ORC.

In a further embodiment, the backing is in the form of a knitted, woven or non-woven fabric.

In a further embodiment, the fibrinogen and/or fibrin containing formulation further comprises thrombin.

In one embodiment the formulation comprises a two-component formulation comprising: a thrombin component, such as, and without being limited thereto, a liquid thrombin component, and a fibrinogen component, such as, and without being limited thereto, a liquid fibrinogen component.

In one such embodiment, the combining comprises one or more steps selected from spraying, smearing, brushing, casting, printing, injecting and soaking the fibrinogen and/or fibrin containing liquid formulation In one embodiment, following the combining, the method comprises a step of pressing the wound dressing against the wounded tissue.

In a further embodiment, the pressing is carried out for a time sufficient to allow adherence of the wound dressing to at least a portion of the wounded tissue.

In a further embodiment, the method is for treating a wound during a surgical procedure.

In a further embodiment, the surgical procedure comprises a procedure selected from abdominal surgery, cardiovascular surgery, thoracic surgery, head and neck surgery, pelvic surgery, and skin and subcutaneous tissue procedure.

In one embodiment, the wounded tissue comprises a bleeding artery.

In one embodiment, the treatment comprises reducing bleeding in a subject, for example, a human subject.

According to another aspect of the present invention there is provided a method of treating a wounded tissue in a subject, the method comprising ex vivo combining a liquid formulation comprising fibrinogen and/or fibrin with an oxidized cellulose backing, such as, and without being limited thereto, ORC backing, to form a wound dressing; and applying the wound dressing onto a wound, the application being carried out within less than 20 seconds from the combining.

In some embodiments, application may be carried out within 19, 18, 17, 16, 15, 14, 13, 12, 11, 10, 9, 8, 7, 6 5, 4, 3, 2, or 1 seconds, or even immediately upon the combining. In some embodiments, the application onto the wound is carried out after at least 2 to 5 seconds from combining, or in some embodiments, after at least 2 to 10 seconds from combining.

In one such embodiment, the backing has a wound facing side and the liquid formulation is combined, with at least the wound facing side or a portion thereof.

The invention provides use of a wound dressing for treating a wound in a subject in need by applying the dressing to the wound, the dressing comprises fibrinogen and/or fibrin containing liquid formulation ex vivo combined with an oxidized cellulose backing, such as, and without being limited thereto, ORC backing, the applying being carried out within less than 20 seconds from combination of the liquid with the backing.

In one such embodiment, the backing or scaffold has a wound facing side and the liquid formulation is combined at least partially with the wound facing side.

In one such embodiment, the wounded tissue is a bleeding tissue.

In one such embodiment, the backing comprises ORC.

In one such embodiment, the backing is in the form of a knitted, woven or non-woven fabric.

In one such embodiment, the fibrinogen and/or fibrin containing formulation further comprises thrombin.

In one such embodiment, the formulation comprises a two-component formulation comprising: a thrombin component, such as, and without being limited thereto, a liquid thrombin component, and a fibrinogen component, such as, and without being limited thereto, a liquid fibrinogen component.

In one such embodiment, the formulation comprises a two-component formulation comprising: a thrombin component, such as, and without being limited thereto, a liquid thrombin component, and a fibrin component, such as, and without being limited thereto, a liquid fibrin component.

In one such embodiment, the combining comprises one or more steps selected from spraying, smearing, brushing, casting, printing, injecting and soaking the fibrinogen and/or fibrin containing liquid formulation In one such embodiment, following the combining, the method comprises pressing the wound dressing against the wounded tissue.

In one such embodiment, the pressing is for a time sufficient to allow adherence of the wound dressing to at least a portion of the wounded tissue.

In one such embodiment, the use is for treating a wound during or following a surgical procedure.

In one such embodiment, the surgical procedure comprises a procedure selected from abdominal surgery, cardiovascular surgery, thoracic surgery, head and neck surgery, pelvic surgery, and skin and subcutaneous tissue procedure.

In one such embodiment, the wounded tissue comprises a bleeding artery.

In one such embodiment, the use comprises reducing bleeding in a subject, for example, a human subject.

In another aspect, there is provided a kit for treating a wounded tissue in a subject, the kit comprising a first container comprising an oxidized cellulose (OC) backing, such as, and without being limited thereto, ORC backing; and a second container comprising fibrinogen and/or fibrin containing formulation, and optionally instructions for use according to the methods disclosed herein.

In one embodiment of the kit, the formulation is in a liquid or in a frozen form.

In a further embodiment of the kit, the backing is in the form of a knitted, woven or non-woven fabric.

In one embodiment, the kit comprises thrombin in a third container.

In one embodiment of the kit, the formulation comprises a two-component formulation comprising: a thrombin component, such as, and without being limited thereto, a liquid thrombin component, and a fibrinogen component, such as, and without being limited thereto, a liquid fibrinogen component.

In one embodiment of the kit, the formulation comprises a two-component formulation comprising: a thrombin component, such as, and without being limited thereto, a liquid thrombin component, and a fibrin component, such as, and without being limited thereto, a liquid fibrin component.

The following description, while describing the invention with reference to the method of preparing the wound dressing, should be read as also describing features of the other aspects of the disclosed invention, including the method of treatment, the wound dressing per se and the kit product.

For the purpose of producing the wound dressing disclosed herein, two main components are utilized, the fibrinogen and/or fibrin containing liquid formulation and the OC backing.

The ex vivo combination of the fibrinogen and/or fibrin containing liquid formulation with an oxidized cellulose backing was found to permit adhesion to the bleeding wound, and thus address hemostasis without being depended by the condition of the wounded tissue, e.g., severity of bleeding.

When referring to ex vivo, in the context of the present disclosure, it should be interpreted as any location that is not in physical contact with the wounded tissue.

The term "fibrinogen and/or fibrin containing liquid formulation" or "(fibrinogen-based sealant formulation") is to be understood as a liquid formulation comprising fibrinogen and/or fibrin which may function as a sealant. This liquid formulation is referred also a biological tissue adhesive formulation, such as formulation of: fibrin glue, fibrin sealant, fibrin adhesive, fibrin film, fibrin network, fibrin lattice, fibrin mesh, fibrin greed and fibrin gel. These formulations thus having ingredients that upon contact with the tissue or blood react to subsequently reduce or stop bleeding and/or seal physiological leaks, e.g., of cerebrospinal fluids (CSF), lymph, bile, gastrointestinal (GI) content, air leak from lungs etc.

In the context of the present disclosure it is further to be understood that during storage the formulation ingredients do not interact with each other and are essentially inert until they are brought into contact with the member of the coagulation cascade. Once the member is activated by the sealant components, clotting initiates and fibrin clot based tissue adhesive is formed.

The fibrinogen component in the formulation may be purified and isolated fibrinogen per se, but also may be biologically active component (BAC) of blood plasma comprising fibrinogen concentrated viral-inactivated cryoprecipitate of human plasma comprising solution of blood plasma derived proteins.

In some embodiments, the fibrinogen is provided as part of the BAC. There are several types of BAC. In some embodiments, BAC is a biologically active component that comprises tranexamic acid, as an antifibrinolytic agent.

In some other embodiments, BAC is a biologically active component that does not contain tranexamic acid. This is considered a second-generation BAC and is referred to in the art as "BAC2". During BAC2 preparation, plasminogen (the enzyme precursor of plasmin, which breaks down fibrinogen and fibrin) and/or plasmin is removed.

In one embodiment, BAC is BAC2, i.e. a biologically active component that lacks tranexamic acid.

BAC may be prepared as component A in the disclosure of EP 534 178. For example, component A therein is prepared from concentrated cryoprecipitate, and undergoes viral inaction by solvent detergent treatment and pasteurization.

In some embodiments, BAC2 is a concentrated viral inactivated cryoprecipitate comprising mainly fibrinogen and is plasminogen-depleted (the removal of plasminogen may be carried out as described in EP 1 390 485). In view of removal of plasmin/plasminogen from the cryoprecipitate, there is no need to add anti-fibrinolytic agents, such as, and without being limited thereto, tranexamic acid, aprotinin or the like.

In some embodiments, fibrinogen is purified from an aluminum hydroxide precipitate [a byproduct from the manufacture process of factor VIII (FVIII)] as disclosed in WO2013001524A1.

The BAC solution may further comprise stabilizers such as, and without being limited thereto, arginine, lysine or other sealant additives as known in the art.

In some embodiments, BAC, optionally BAC2, may be derived from cryoprecipitate (in particular concentrated cryoprecipitate).

Herein, unless otherwise stated, when referring to BAC it is to be understood as preferably, but not exclusively, referring to BAC2.

Examples of fibrinogen sources include, but are not limited to, recombinant fibrinogen, purified fibrinogen, and fibrinogen component.

In some embodiments, the fibrinogen and/or fibrin containing liquid formulation is provided as a part of a two-component formulation that are to be blended together prior to use. Some such two components include a first, fibrinogen-containing component, and a second, thrombin-containing component.

In some embodiments, for the purpose of producing the wound dressing disclosed herein, three main components are utilized: (i) a fibrinogen containing component, (ii) a thrombin containing component, and (iii) an OC backing, such as, and without being limited thereto, ORC backing.

In some embodiments, for the purpose of producing the wound dressing disclosed herein, a two-component fibrin sealant formulation is used together with an OC backing, such as, and without being limited thereto, ORC backing. In some embodiments, the fibrin sealant formulation comprises a fibrinogen containing component and a thrombin containing component.

There are various commercially available fibrinogen-based sealant formulations. For example, the sealant formulation is one comprising fibrinogen and thrombin, such as, and without being limited thereto, the FDA approved sealant, marketed under the trademark EVICEL®, is a package containing one vial each of BAC2 (55-85 mg/ml BAC2) and thrombin (800-1200 IU/ml human thrombin) frozen solutions.

A further commercially available sealant is the FDA approved product marketed under the tradename TISSEEL®. TISSEEL is a fibrin sealant provided, as a two-component fibrin sealant comprising freeze-dried Sealer Protein Concentrate (fibrinogen and aprotinin) and thrombin that are reconstituted in fibrinolysis inhibitor solution and calcium chloride solution, respectively.

In some other embodiments, the formulation is a one/single component sealant (glue) formulation comprising fibrinogen, calcium ion and factor XIa such as that described in PCT patent application No. PCT/IL2017/000006.

In some other embodiments, the fibrinogen and/or fibrin containing formulation is an aqueous formulation. When referring to an "aqueous formulation" it is to be understood to encompass a blend of ingredients, in liquid or frozen, that contains water molecules. In some embodiments, the aqueous formulation is in liquid form. When in liquid form, it is in accordance with some embodiments that the liquid carrier is a buffer having an essentially neutral pH, e.g., pH 7.0±0.5.

In some embodiments, the formulation is frozen. Prior to use, the formulation may be thawed and thereby turn into liquid form at room temperature.

In yet some other embodiments, the formulation is in the form of a powder e.g., lyophilized and prior to use the powder is moistened with an aqueous solution.

As described hereinthroughout, in the context of the present disclosure, the oxidized cellulose (OC) backing also encompasses oxidized regenerated cellulose (ORC) backing.

In some embodiments, the OC backing may be combined with other substances typically used as TAH, such as, any one or combination of gelatin, collagen, chitin and chitosan.

In one embodiment, OC is present in the wound facing side whereas the other substances typically used as TAH such as, and without being limited thereto, any one or combination of gelatin, collagen, chitin and chitosan are present in the side that is not facing the wound.

In some embodiments, the OC backing is not combined with other substances typically used as TAH, such as, any one or combination of gelatin, collagen, chitin and chitosan.

When referring to "backing" it is to be understood as meaning a physical structure, e.g. scaffold or patch made of at least OC. In some embodiments, the backing is in the form of a fabric. The fabric may be in a knitted, woven or non-woven form.

As used herein, the term "patch" relates to a piece of material used to protect a part of the body, give shape to something or clean something, and is intended to include a pad, a cloth, a mesh, a dressing, a gauze, and the like.

As used herein, the term "pad" relates to a small piece of material that can be sewn or otherwise attached over a surface or wound.

As used herein, the term "cloth" relates to woven or felted fabric made from a fiber.

As used herein, the term "mesh" relates to a material made of a network of connected strands of flexible materials such as wire or thread.

As used herein, the term "dressing" relates to a covering for a wound.

As used herein, the term "fabric" relates to a flexible material comprising a network of fibers produced by weaving, knitting, crocheting, knotting, felting or bonding.

As used herein, the term "gauze" relates to thin, loosely woven cloth used for dressings and swabs or to any material made of an open, mesh-like weave.

The OC backing may provide a scaffold for the formation of the wound dressing.

In some embodiments, the "backing" is in the form of a powder, e.g. OC powder.

Some of the most commonly used OC backing materials (topical hemostatic agents) belong to the family of agents marketed under the tradename SURGICEL®. These are made from oxidized regenerated cellulose (ORC). The SURGICEL® family of absorbable hemostats comprising four main product groups, with all hemostatic wound dressings commercially available from Ethicon, Inc., Somerville, N.J., a Johnson & Johnson Company.

SURGICEL® Original hemostat is a white fabric with a pale-yellow cast and a faint, caramel like aroma. This material is strong and may be sutured or cut without fraying. Further, is a loose knit ORC fabric that conforms rapidly to its immediate surroundings and is easy to manage because it does not stick to surgical instruments and its size may be easily trimmed. This allows the surgeon to hold the cellulose firmly in place until all bleeding stops. The control of bleeding is essential and critical in surgical procedures to minimize blood loss, to reduce post-surgical complications, and to shorten the duration of the surgery in the operating room. Due to its biodegradability and its bactericidal and hemostatic properties, oxidized cellulose, as well as oxidized regenerated cellulose have long been used as a topical hemostatic wound dressing in a variety of surgical procedures.

One member of the family is SURGICEL® NU-KNIT® absorbable hemostat, which is similar to SURGICEL® Original but has a denser knit and thus a higher tensile strength, this material is particularly recommended for use in trauma and transplant surgery as it may be wrapped or sutured in place to control bleeding;

SURGICEL® FIBRILLAR™ absorbable hemostat product form has a layered structure that allows the surgeon to peel off and grasp with forceps any amount of material needed to achieve hemostasis at a bleeding site, and therefore, may be more convenient than the knitted form for hard to reach or irregularly shaped bleeding sites. It is particularly recommended for use in orthopedic/spine and neurological surgery;

SURGICEL® SNoW™ absorbable hemostat product form is a structured non-woven fabric that may be more convenient than other forms for endoscopic use due to the structured, non-woven fabric, and is highly adaptable and recommended in both open and minimally invasive procedures.

Typically, SURGICEL is a non-abrasive textured rayon fabric with a white to pale yellow cast. It has a Carboxyl Content of 18-21%. The knit structure varies depending on the product:

SURGICEL Original—is a knitted material;
NUKNIT—is a further kind of a knitted material;
SURGICEL® FIBRILLAR™—Nonwoven;
SNoW—Light Nonwoven.

In some embodiments, the OC backing is INTERCEED™ is a non-abrasive textured rayon fabric with a white to pale yellow cast. It has a Carboxyl Content of 12-18%. INTERCEED™ is a knitted material.

Typically, "nonwoven fabric" is used in the textile manufacturing industry to denote fabrics, such as, and without being limited thereto, felt, which are neither woven nor knitted.

Typically, the term "nonwoven fabric" includes, but is not limited to, bonded fabrics, formed fabrics, or engineered fabrics, that are manufactured by processes other than spinning, weaving or knitting. The structure of the nonwoven fabric is based on the arrangement of, for example, staple fibers that are typically arranged more or less randomly. Notwithstanding, the raw materials used to manufacture the nonwoven fabric may be yarns, scrims, netting, or filaments made by processes that include spinning, weaving or knitting (as disclosed in EP1802358A2).

In some embodiments, the OC backing has a face with which fibrinogen and/or fibrin is combined. This face is referred to as the "wound facing side" of the backing.

According to the present disclosure, the wound dressing is produced by combining, at a location remote from the tissue to be treated with the dressing, the fibrinogen and/or fibrin-containing liquid formulation with an oxidized cellulose (OC) backing, the combining includes at least applying or providing the fibrinogen and/or fibrin containing formulation to the wound facing side of the backing.

The combining of the OC backing and the fibrinogen and/or fibrin containing formulation may be by any means known in the art. These include, without being limited thereto, application at least onto a side designated as the wound facing side of the backing, by spraying, smearing, brushing, casting, printing, injecting, soaking, coating and any combination of same.

Without being bound by theory, it appears that the sealant components crosslink and adhere to the wound, creating a frail liquid-tight barrier which is supports by the TAH backing. The sealant components also crosslink within the porous OC fibers/TAH, mechanically locking the OC to the formed liquid-tight barrier.

The formation of the sealant (biological glue) occurs in a relatively short period of time subsequent to the combination of the liquid formulation and the OC backing. It has been found that there is a narrow time window suitable for the combination of components and application onto the wound that provides a superior adhesiveness to the resulting dressing in comparison to other time windows.

In addition, the combination according to the invention was found to be advantageous in cases of severe bleeding where application of the sealant directly onto the wound side could be washed away/diluted, as further addressed below.

As shown in the following non-limiting examples, it has been found that the application of the wound dressing onto the wound should be within less than 20 seconds from the time of combination, i.e. with a minimal cross-linking time of less than 20 seconds.

This combination of the liquid formulation and the OC backing ex vivo provides the wound dressing that is then applied onto the wound.

In some embodiments, the wound dressing is particularly advantageous when applied onto severely bleeding wounds, i.e. when the flow of blood and/or other bodily fluids from the wound is intense.

In some embodiments, the placing of the ex vivo formed wound dressing is within any time point from the second of its production by combining the fibrinogen and/or fibrin-containing liquid formulation with the OC backing, and until 19 seconds, at times, until 18, at times, until 17, at times, until 16, at times, until 15, at times, until 14, at times, until 13, at times, until 12, at times, until 11, at times, until 10, at times, until 9, at times, until 8, at times, until 7, at times, until 6, at times, until 5, at times, until, 4, at times, or until 3 seconds from the moment of combination. In some embodiments, the application onto the wound is after at least 2-5 seconds from preparation, at times, after at least 2-10 seconds from preparation.

Once the wound dressing is produced, it is applied onto the wound. In some embodiment, this involves pressing it against the target/wounded tissue.

In some specific embodiments, the wounded tissue comprises a bleeding artery.

The wound dressing is pressed for a time sufficient to allow adherence of the wound dressing to at least a portion of the wounded tissue. In this manner, the combined effect of the formed fibrin glue and the clotted blood of the subject can assist in controlling the bleeding of the wounded tissue.

In some embodiments, the wound dressing is pressed against the wound until bleeding is essentially stopped.

The methods disclosed herein and the produced wound dressing may be used for treating various animal tissues. In this context, the animal may be a human as well as a non-human animal.

In some embodiments, the animal is a mammal.

In some embodiments, the animal is a human subject.

Treatment with the wound dressing disclosed herein can be given during any standard procedure, e.g. personal care (i.e. at home), in a clinic, during a surgical procedure etc.

There are many surgical procedures in which the wound dressing of the present disclosure can be used, such as, without being limited thereto, abdominal surgery, cardiovascular surgery, thoracic surgery, head and neck surgery, pelvic surgery, skin and subcutaneous tissue procedure.

To facilitate production of the wound dressing, the components thereof, namely, the fibrinogen containing formulation (be it a two-component formulation or a single component formulation as described above) and the OC backing can be provided as separate components within a commercial kit. To this end, the kit, e.g. including a label for use in wound treatment, contains a first container/package including the fibrinogen formulation, and a second container/package containing the OC backing.

The fibrinogen containing formulation may be stored in liquid or frozen form such that, for example, it may be preserved for a long period when it is in its frozen form and thawed just before use.

In some embodiments, the kit is provided with instructions for use of the OC backing in combination with the fibrinogen and/or fibrin containing formulation for the ex vivo production of the wound dressing and application thereof onto the wound.

In some embodiments, the instructions comprise applying of the thus formed wound dressing at a time interval of less than 20 seconds (as defined hereinabove) from the moment of the combination.

As used herein the term "about" refers to ±10%.

The terms "comprises", "comprising", "includes", "including", "having", and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

In the following non-limiting Example, cross linking time and adhesion intensity of the wound dressing disclosed herein was examined in an ex-vivo model.

Example 1

Adhesion Intensity in an Ex-Vivo Model

Materials:

Porcine skin tissue with exposed dermis was received from Lahav contract research organization (C.R.O.) and delivered in chilled containers (4° C.).

For the application of the fibrin sealant, the EVICEL® airless spray accessory tip was assembled on top of a 5 ml EVICEL® device.

EVICEL® is a package containing one vial each of BAC2 (55-85 mg/ml BAC2) and thrombin (800-1200 IU/ml human thrombin).

In exemplary procedures (including Example 2), the BAC2 component and the thrombin component are combined at ratio of 1:1 (v/v) (and are therefore diluted accordingly.)

When EVICEL® was applied, either directly on the tissue or on SURGICEL®, 1 ml of the fibrin sealant was used.

When SURGICEL® was applied, SURGICEL NU-KNIT® was cut to a 5.08 cm×5.08 cm patch size to be used either as a control or with combination of EVICEL®.

Adhesion Intensity Ex-Vivo Model:

Porcine skin tissue was used to evaluate the adhesion intensity of a wound dressing prepared from a fibrin sealant and an ORC patch and applied to tissue in accordance with the Method of the present disclosure vis-à-vis the reference method (as described below).

Method of the present disclosure: fibrin sealant EVICEL® was applied on the ORC patch SURGICEL NU-KNIT® and the combined product was applied, jointly, onto the porcine skin tissue.

Reference Method: the fibrin sealant EVICEL® was applied on the porcine skin tissue followed by the application of the ORC patch SURGICEL NU-KNIT® on top of EVICEL®.

Also, in this study, the effect of EVICEL® crosslinking time ("curing time") on the adhesion intensity was examined. To this end, once the fibrin sealant was applied, either on SURGICEL® or directly onto the tissue, the adhesion intensity at different "curing times" was determine.

Method:

Porcine skin tissue was placed dermis side facing up and hydrated using saline (0.9%) soaked gauze to keep the tissue moist when necessary. 1 ml of fibrin sealant EVICEL® was applied in combination with a 5.08 cm×5.08 cm patch of SURGICEL NU-KNIT® on the dermis. EVICEL® was either applied directly on the tissue followed by the application of SURGICEL®, or, EVICEL® was applied on SURGICEL® followed by their joined application to the tissue.

To examine the effect of EVICEL® crosslinking time ("curing time") on the adhesion intensity, Fibrin sealant was applied, either on SURGICEL® or on the tissue, and two "curing times" were taken (immediately, i.e. at time of around 0 seconds and at 20 seconds from the application of EVICEL® to the tissue or to the SURGICEL® pad).

At the specified time, the ORC patch (with or without the fibrin sealant) was applied onto the skin. After two minutes in situ, the dressing (patch with fibrin sealant) was pulled from the tissue using forceps and the adhesion intensity was manually assessed on a scale of 0-5; whereby no adhesion was given a score of 0 and intensive adhesion was given a score of 5. As a control, the adhesion force of SURGICEL® without EVICEL® was also measured.

Results:

The fibrin sealant (fibrin glue) was either applied directly on the tissue followed by the application of the ORC patch (Reference Method), or, the fibrin sealant (fibrin glue) was applied on the ORC patch followed by the coated patch application on the tissue (Method disclosed herein).

Different crosslinking/curing times were taken at which the patch's adhesion intensity to the tissue was assessed on a scale of 0-5. As a control, the adhesion force of SURGICEL® without EVICEL® was also measured.

Figure 1:
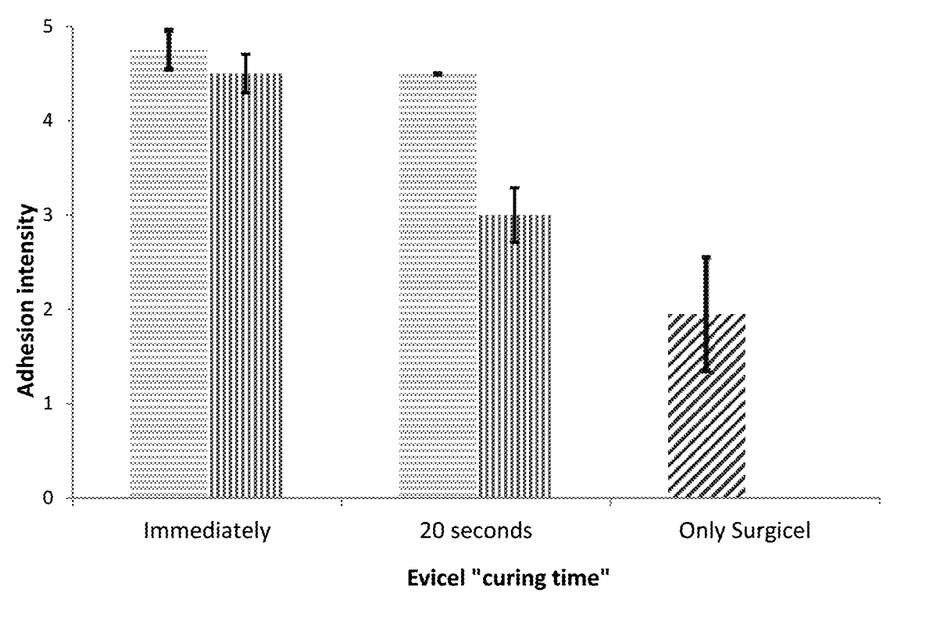
FIG. 1 is a bar graph showing the adhesion intensity of a wound dressing prepared ex vivo with crosslinking (curing) times of around 0 (immediately) and after 20 seconds. For each crosslinking time, right-hand bars (vertical stripes) represent Evicel® drip on pad preparation according to the invention, while the left-hand bars (horizontal stripes) represent in situ preparation of Evicel® drip directly on tissue, as described in Example 1. The right-most bar (diagonal stripes, only Surgicel) represents ORC only. Error bars represent standard deviation.

The results are shown in FIG. 1. Specifically, FIG. 1 presents, in the form of a bar graph, the strength required in order to remove the patch, namely the wound dressing, from the tissue.

The most left bars identified as "immediately" show that when the combined patch/fibrin sealant is applied by either method to the tissue, almost the same amount of force is required in order to remove/peal the patch from the tissue. However, as also shown, it is essential that when the combination takes place ex vivo, the application of the combined patch has to be in less than 20 seconds, otherwise the intensity of adhesion is reduced.

In other words, the results in FIG. 1 demonstrate no statistical significant between the application techniques when they are immediately applied. This demonstrate how the novel technique is at least an equivalent method with regards to adherence strength. However, statistical significant can be found when the patch including the combined patch/fibrin sealant application is carried out 20 second after the fibrin sealant application. This demonstrates the importance of timing in the application method.

Thus, while there is an advantage of combining the fibrin formulation with the backing ex vivo (there is no washing off of the formulation by the bleeding wound, e.g. in cases of severe bleeding), this has to be done in less than 20 seconds so as to retain the strength/adherence of the dressing.

Example 2

Adhesion Intensity in an In-Vivo Model

The in vivo efficacy of Fibrin sealant applied on an ORC patch SURGICEL NU-KNIT® was examined next.

The test articles were prepared by the application of fibrin sealant 1 ml to an ORC patch (5.08 cm×5.08 cm). Next, various crosslinking times (crosslinking time being defined as time from application of the fibrin sealant to the ORC until application of the test article to the defect site) were allowed for the applied fibrin sealant following the test article application to the defect site. The examined crosslinking times were: around 0 seconds (immediately), after 10 seconds and after 20 seconds of crosslinking time.

The animal procedure used is based on the procedure previously reported in MacDonald et al. 2017, Medical Devices: Evidence and Research 10: 273-279, with the following modifications:

a disposable biopsy punch of 8 mm with a stop set to 2 mm was used;

a tamponade was applied for 30 seconds after the test article application and the presence of free-flowing blood was monitored for 2 minutes;

Briefly, a ventral midline abdominal incision was performed in a porcine and the cranial portion of the midline incision was extended to improve exposure of the liver. The liver was positioned as necessary to maximize testing surface availability. The abdominal organs were kept moist with saline and saline-soaked laparotomy sponges throughout the procedure. The liver parenchymal defects were created on the diaphragmatic surface of accessible areas of the left, right, and quadrate lobes using a disposable 8 mm biopsy punch with a depth stop set to 2 mm. The core portion of the biopsy was grasped and sharply dissected free from the underlying surface causing mild to moderate hemorrhage.

The defect site was allowed to bleed for several seconds prior to product application to allow for characterization of the resulting hemorrhage. The trial site was blotted with gauze and then one of the test articles was applied. For the purposes of this study, effective hemostasis was defined as the cessation of free flow bleeding. Pinpoint or petechial bleeding that appeared but did not grow was not considered to be free flow bleeding. The test article was prepared and then applied onto the defect (bleeding site) manually. Tamponade was applied for 30 seconds using digital pressure on a gauze. Following the initial 30 seconds of tamponade, the dressing was removed. If hemostasis was not achieved after 120 seconds, the test article was determined as unable to achieve effective hemostasis. The efficacy results of the fibrin sealant applied (EVICEL®) on an ORC patch (SURGICEL® pad), following their application to the defect site with different crosslinking times are displayed in Table 1.

TABLE 1 in vivo hemostasis efficacy of fibrin sealant applied to an ORC patch with different crosslinking times

| Crosslinking times | Hemostasis achieved (Yes/No) |
|---|---|
| Around 0 seconds (immediate application) | Yes |
| 10 seconds | Yes |
| 20 seconds | No |

The results demonstrate that the effective hemostasis can be achieved by fibrin sealant application to ORC followed by their combined application to the defect site, but only if the allowed crosslinking time is below 20 seconds in this porcine model.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method for producing a wound dressing to be applied onto a tissue, the method comprising:
   (a) ex vivo combining a first liquid formulation comprising fibrinogen and thrombin with a second liquid formulation comprising fibrin to obtain a sealant comprising fibrinogen, thrombin and fibrin, and
   (b) contacting the sealant with an oxidized cellulose (OC) backing to thereby obtain the wound dressing comprising said sealant;
   wherein the wound dressing is to be applied to a tissue within less than 20 second from said combining.

2. The method of claim 1, wherein said OC backing has a wound facing side and said sealant is contacted at least partially, with said wound facing side.

3. The method of claim 1, wherein the OC backing comprises oxidized regenerated cellulose (ORC).

4. The method of claim 1, wherein said thrombin is present at a concentration ranging from 400 to 1200 IU/ml, and wherein said fibrinogen and/or fibrin are present at a concentration ranging from 10 to 120 mg/ml.

5. A method of treating a wounded tissue in a subject, the method comprising:
   (a) ex vivo combining a first liquid formulation comprising fibrinogen and thrombin with a second liquid formulation comprising fibrin to obtain a sealant comprising fibrinogen, thrombin and fibrin,
   (b) contacting the sealant with an oxidized cellulose (OC) backing to thereby obtain the wound dressing comprising said sealant; and
   (c) applying the wound dressing onto a wound, said applying being within less than 20 seconds from said combining.

6. The method of claim 5, wherein said OC backing has a wound facing side and said sealant is contacted at least partially, with said wound facing side, and wherein said wound facing side is applied onto said wounded tissue.

7. The method of claim 5, wherein said wounded tissue is a bleeding tissue.

8. The method of claim 5, wherein the OC backing comprises oxidized regenerated cellulose (ORC).

9. The method of claim 5, further comprising pressing said wound dressing against the wounded tissue.

10. The method of claim 5, for treating a wound during a surgical procedure.

11. The method of claim 5, wherein the treatment comprises reducing bleeding.

* * * * *